US00PP09532P

United States Patent [19]

Trees

[11] Patent Number: Plant 9,532

[45] Date of Patent: Apr. 30, 1996

[54] NEW GUINEA IMPATIENS NAMED BFP-368 ROSE

[75] Inventor: Scott C. Trees, Arroyo Grande, Calif.

[73] Assignee: Geo. J. Ball, Inc., West Chicago, Ill.

[21] Appl. No.: 422,691

[22] Filed: Apr. 14, 1995

[51] Int. Cl.[6] ..... A01H 5/00

[52] U.S. Cl. ..... Plt./87.6

[58] Field of Search ..... Plt./87.6

*Primary Examiner*—James R. Feyrer

*Attorney, Agent, or Firm*—Burns, Doane, Swecker & Mathis

[57] ABSTRACT

A new and distinct New Guinea Impatiens cultivar named 'BFP-368 Rose' is provided. This new cultivar was the result of a controlled breeding program wherein a plant designated N2507-3 (non-patented in the United States) was pollinated by a plant designated 3616-A (non-patented in the United States). The new cultivar forms large round rose colored flowers which exhibit an iridescent appearance, forms medium green foliage, exhibits a good basal branching character and displays a medium upright growth habit. The new cultivar can be readily distinguished from the 'Kallima' cultivar (non-patented in the United States).

1 Drawing Sheet

SUMMARY OF THE INVENTION

The present invention comprises a new and distinctive Impatiens plant, botanically known as New Guinea Impatiens, and hereinafter is referred to by the cultivar name 'BFP-368 Rose'.

The new cultivar is the product of a planned breeding program. More specifically, the breeding program which resulted in the production of the new cultivar was carried out in a controlled environment during 1992 at Arroyo Grande, Calif., U.S.A. The female parent (i.e., the seed parent) was a plant designated N2507-3 (non-patented in the United States) which exhibits bright salmon flowers with medium green foliage. The male parent (i.e., the pollen parent) was a plant designated 3616-A (non-patented in the United States) which exhibits very large rose pink flowers, and dark green foliage. The parentage of the new cultivar can be summarized as follows:

N2507-3×3616-A.

The seeds resulting from the above pollination were sown and plantlets were obtained which were physically and biologically different from each other. Selective study resulted in the identification of a single plant of the new cultivar. This plant had large rose colored flowers and initially was designated BFP-368. Another progeny of the same cross has been named 'Raspberry Rose' (U.S. Plant patent application Ser. No. 338,155, filed Nov. 8, 1994) now U.S. Plant Pat. No. 9,212.

It was found that the new cultivar of the present invention:

(a) exhibits attractive large dark rose colored flowers, (b) forms medium green foliage, (c) exhibits a good basal branching character, and (d) exhibits a medium upright growth habit.

Asexual reproduction of the new cultivar by terminal or stem cuttings taken during 1992, at Arroyo Grande, Calif., U.S.A., has demonstrated that the characteristics of the new cultivar as herein described are firmly fixed and are retained through successive generations of such asexual propagation.

The 'BFP-368 Rose' cultivar has not been observed under all possible environmental conditions to date. Accordingly, it is possible that the phenotype may vary somewhat with variations in the environment, such as temperature, light intensity, and day length.

When the new cultivar of the present invention is compared to the 'Kallima' cultivar (non-patented in the United States), it is found that the new cultivar exhibits a slightly less compact growth habit (e.g., approximately 8 to 10 cm.×approximately 24 to 29 cm. vs. approximately 7 to 9 cm.×approximately 22 to 25 cm.), forms larger flowers (e.g., approximately 7.0 to 7.5 cm.×approximately 6.4 to 7.2 cm. vs. approximately 6.6 to 7.0 cm.×approximately 6.0 to 6.2 cm.), and forms larger leaves (e.g., approximately 13 to 15 cm.×approximately 4.5 to 5.5 cm. vs. 10 to 12 cm.×approximately 3.2 to 3.6 cm.).

When plant material of the 'BFP-368 Rose' cultivar is subjected to standard random amplified polymorphic DNA marker analysis (RAPD) using polymerase chain reaction (PCR) and a known unique set of DNA primers, it is found to exhibit a different fingerprint map when compared to that of the 'Kallima' cultivar which confirms its genetic distinctiveness.

Plants of the new cultivar will be marketed under the Celebration trademark by Geo. J. Ball, Inc.

BRIEF DESCRIPTION OF THE PHOTOGRAPH

The accompanying photograph of FIG. 1 shows as nearly true as it is reasonably possible to make the same in a color illustration of this character, a typical specimen of an overall plant of the new cultivar. Typical flower and foliage characteristics are illustrated. The plant was grown in a greenhouse at West Chicago, Ill., U.S.A.

DETAILED DESCRIPTION

Figure 1:
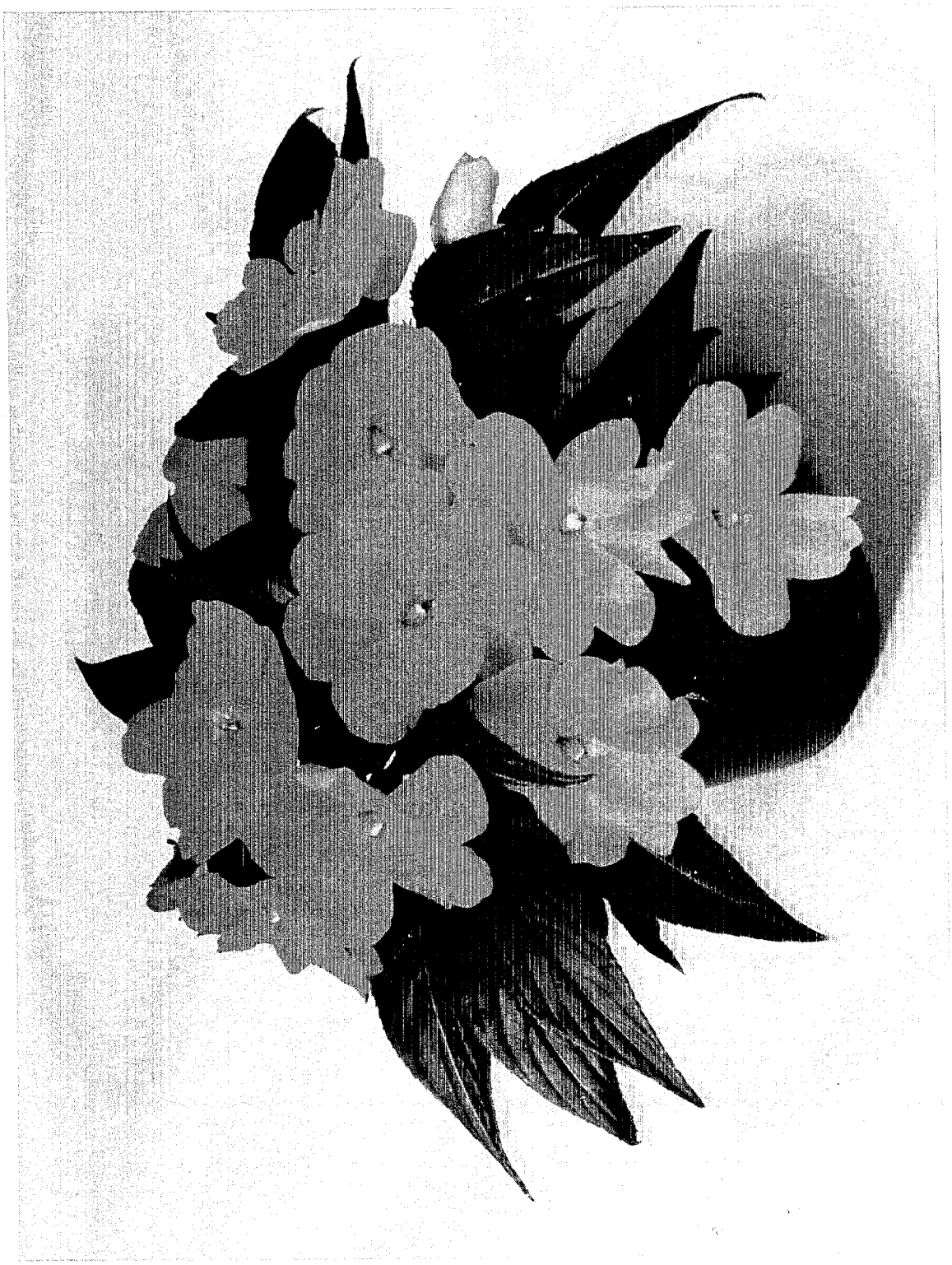

The chart used in the identification of colors described herein is the R.H.S. Colour Chart of The Royal Horticultural Society, London, England. The color values were determined on Jan. 3, 1995. The readings were taken between 1:00 and 1:45 p.m. under 2,000 footcandles of light at West Chicago, Ill., U.S.A. The plants were produced from cuttings taken from stock plants and were grown under greenhouse conditions comparable to those used in commercial practice while utilizing a soilless growth medium and maintaining temperatures of approximately 72° F. during the day and approximately 65° F. during the night.

Propagation:

*Type cutting.*—Terminal tip.

*Time to initiate roots.*—Approximately 14 to 21 days with the shorter times generally being experienced in the summer and the longer times in the winter.

Rooting habit.—Fibrous, and branching.

Plant description:

*Habit of growth.*—Basal branching.

*Form.*—Medium upright mounded. A mature plant commonly measures approximately 8 to 10 cm. in height and approximately 24 to 29 cm. in width. This can be compared to a height of approximately 7 to 9 cm. and a width of approximately 22 to 25 cm. for the 'Kallima' cultivar.

*Foliage.*—The configuration is narrow and lanceolate. The leaves commonly measure approximately 13 to 15 cm. in length and approximately 4.5 to 5.5 cm. in width. This can be compared to a length of approximately 10 to 12 cm. and a width of approximately 3.2 to 3.6 cm. for the 'Kallima' cultivar. The foliage of the new cultivar is Yellow-Green Group 147A (adaxial) and Yellow-Green Group 147B (abaxial). This can be compared to Green Group 136A with midrib of Red-Purple Group 60A (adaxial) and Greyed-Purple Group 187A (abaxial) for the 'Kallima' cultivar. The stem color is Green Group 143B for the new cultivar. This can be compared to Greyed-Purple Group 185A for the 'Kallima' cultivar.

Flower description:

*Flowering habit.*—Freely flowering.

*Natural flowering season.*—Throughout the year in a greenhouse environment.

*Flowers borne.*—Above the foliage arising from leaf axils.

*Flower color.*—Red-Purple Group 58B (adaxial) and Red-Purple Group 58D (abaxial). This can be compared to Red-Purple Group 73B with attachment points of Red-Purple Group 66A (adaxial) and Red-Purple Group 73C with midrib of Red-Purple Group 66A (abaxial) for the 'Kallima' cultivar.

*Quantity of flowers.*—Approximately 5 to 7 per stem which can be compared to approximately 5 to 8 per stem for the 'Kallima' cultivar.

*Number of petals.*—Five.

*Flower size.*—Approximately 7.0 to 7.5 cm. in length and approximately 6.4 to 7.0 cm. in width. This can be compared to a length of approximately 6.6 to 7.0 cm. and a width of approximately 6.0 to 6.2 cm. for the 'Kallima' cultivar.

Nectary length.—Approximately 4.2 to 4.7 cm. which can be compared to approximately 5.5 to 6.0 cm. for the 'Kallima' cultivar.

Nectary color.—Red Group 51D which can be compared to Red Group 53C for the 'Kallima' cultivar.

*Reproductive organs.*—The anthers are fused together forming one organ that surrounds the pistil. Generally, the anthers shed pollen prior to the stigma becoming receptive. The pollen color is Yellow Group 12D, and the stigma color is Yellow-Orange Group 14D for both the 'BFP-368 Rose' and 'Kallima' cultivars. The ovary color is Green Group 143B for the 'BFP-368 Rose' cultivar and Red-Purple Group 59A for the 'Kallima' cultivar.

I claim:

1. A new and distinct cultivar of New Guinea Impatiens plant named 'BFP-368 Rose' substantially as herein shown and described, which:

(a) exhibits attractive large dark rose colored flowers, (b) forms medium green foliage, (c) exhibits a good basal branching character, and (d) exhibits a medium upright growth habit.

* * * * *